United States Patent
Bechtel et al.

(10) Patent No.: US 12,205,716 B2
(45) Date of Patent: Jan. 21, 2025

(54) VERIFICATION MANAGEMENT OF PATIENT REQUESTS FOR ASSISTANCE IN A HEALTHCARE FACILITY

(71) Applicant: CERNER INNOVATION, INC., North Kansas City, MO (US)

(72) Inventors: Todd Bechtel, Overland Park, KS (US); Chad G. Hays, Overland Park, KS (US); Amanda Sleightholm, North Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

(21) Appl. No.: 17/950,692

(22) Filed: Sep. 22, 2022

(65) Prior Publication Data
US 2023/0014157 A1    Jan. 19, 2023

Related U.S. Application Data

(62) Division of application No. 16/550,842, filed on Aug. 26, 2019.
(Continued)

(51) Int. Cl.
*G16H 40/63* (2018.01)
*G10L 13/00* (2006.01)
(Continued)

(52) U.S. Cl.
CPC ............. *G16H 40/63* (2018.01); *G10L 13/00* (2013.01); *G10L 15/22* (2013.01); *G10L 15/26* (2013.01);
(Continued)

(58) Field of Classification Search
CPC ........ G16H 40/63; G16H 40/20; G10L 13/00; G10L 15/22; G10L 15/26
See application file for complete search history.

(56) References Cited

U.S. PATENT DOCUMENTS 7,088,235 B1    8/2006  Carricut
2002/0077841 A1 *  6/2002  Thompson ......... A61N 1/37247
                                                              705/2
(Continued)

OTHER PUBLICATIONS

Pre interview First Office Action received for U.S. Appl. No. 16/550,842, mailed on Oct. 4, 2022, 4 pages.
(Continued)

*Primary Examiner* — William L Bashore
*Assistant Examiner* — Gregory A Distefano
(74) *Attorney, Agent, or Firm* — Kraguljac Law Group, LLC (57) ABSTRACT

Systems and methods are provided for managing patient assistance requests in a healthcare facility, documenting items (e.g., minor, routine, and/or frequently-performed items) in association with a patient's records in an Electronic Healthcare Information System, and cancelling patient requests for assistance. Indications that requests for assistance have been received and/or are being addressed by an appropriate healthcare team member may be audibly output from a speaker associated with a personal assistant device. Healthcare team members may verbally provide items for documentation in association with a patient's medical records, the items for documentation being received by a listening component of a personal assistant device and transmitted to an EHIS for documentation. Healthcare team members may verbally cancel patient requests for assistance upon the healthcare team member addressing the request and, in some instances, verification of the healthcare team member as an approved source for documenting the item(s) in association with the patient.

14 Claims, 4 Drawing Sheets

Related U.S. Application Data (60) Provisional application No. 62/722,623, filed on Aug. 24, 2018.

(51) Int. Cl.
- *G10L 15/22* (2006.01)
- *G10L 15/26* (2006.01)
- *G16H 40/20* (2018.01)

(52) U.S. Cl.
CPC ....... *G16H 40/20* (2018.01); *G10L 2015/223* (2013.01)

(56) References Cited

U.S. PATENT DOCUMENTS

| | | |
|---|---|---|
| 2003/0093300 A1 | 5/2003 | Denholm |
| 2005/0234741 A1* | 10/2005 | Rana ................ G06Q 10/107 705/2 |
| 2007/0265533 A1 | 11/2007 | Tran |
| 2009/0214009 A1 | 8/2009 | Schuman, Sr. et al. |
| 2012/0278104 A1* | 11/2012 | Traughber ........ H04M 1/72409 705/2 |
| 2013/0046543 A1* | 2/2013 | Kitchens ................ G16H 10/60 704/270.1 |
| 2015/0106085 A1* | 4/2015 | Lindahl .................. G10L 15/32 704/231 |
| 2015/0106092 A1 | 4/2015 | Nolte et al. |
| 2015/0186829 A1* | 7/2015 | Khan ................ G06Q 10/103 705/7.15 |
| 2015/0294089 A1 | 10/2015 | Nichols |
| 2015/0302539 A1* | 10/2015 | Mazar .................... G08B 21/02 705/3 |
| 2016/0055299 A1 | 2/2016 | Yarnell |
| 2016/0267752 A1 | 9/2016 | Traughber et al. |
| 2017/0011195 A1 | 1/2017 | Arshad |
| 2017/0065757 A1 | 3/2017 | Tanenbaum et al. |
| 2018/0144814 A1 | 5/2018 | Bright |
| 2019/0122760 A1 | 4/2019 | Wang |
| 2019/0122766 A1* | 4/2019 | Strader ................ G06F 16/3344 |
| 2019/0279647 A1* | 9/2019 | Jones ...................... G10L 21/18 |
| 2020/0066402 A1 | 2/2020 | Bechtel et al. |

OTHER PUBLICATIONS

United States Patent and Trademark Office (USPTO), Non-Final Office Action issued in U.S. Appl. No. 16/550,842 having a Date of Mailing of Feb. 3, 2023 (12 pgs).

United States Patent and Trademark Office (USPTO), Non-Final Office Action issued in U.S. Appl. No. 17/950,715 having a Date of Mailing of Mar. 20, 2023 (15 pgs).

United States Patent and Trademark Office (USPTO), Final Office Action issued in U.S. Appl. No. 16/550,842 having a Date of Mailing of Jun. 26, 2023 (17 pgs).

United States Patent and Trademark Office (USPTO), Final Office Action issued in U.S. Appl. No. 17/950,715 having a Date of Mailing of Sep. 29, 2023 (13 pgs).

United States Patent and Trademark Office (USPTO), Notice of Allowance issued in U.S. Appl. No. 16/550,842 having a Date of Mailing of Nov. 1, 2023 (6 pgs).

United States Patent and Trademark Office (USPTO), Notice of Allowance issued in U.S. Appl. No. 17/950,715 having a Date of Mailing of Feb. 14, 2024 (7 pgs).

* cited by examiner

VERIFICATION MANAGEMENT OF PATIENT REQUESTS FOR ASSISTANCE IN A HEALTHCARE FACILITY

CROSS-REFERENCE TO RELATED APPLICATIONS

This application is a divisional of co-pending U.S. Nonprovisional application Ser. No. 16/550,842, filed on Aug. 26, 2019 and entitled MANAGING PATIENT REQUESTS FOR ASSISTANCE IN A HEALTHCARE FACILITY, which claims the benefit of and priority to U.S. Provisional Patent Application No. 62/722,623, filed Aug. 24, 2018 and entitled MANAGING PATIENT REQUESTS FOR ASSISTANCE IN A HEALTHCARE FACILITY, which are hereby incorporated by reference in their entireties. This divisional application is related by subject matter to U.S. Nonprovisional application Ser. No. 17/950,715, filed on Sep. 22, 2022 and entitled CANCELLATION MANAGEMENT OF PATIENT REQUESTS FOR ASSISTANCE IN A HEALTHCARE FACILITY.

BACKGROUND

On a typical shift, members of a patient's healthcare team generally are attending to a number of patients, as well as performing other tasks such as documenting actions in patient charts, consulting with other healthcare team members, counseling patients' loved ones, and the like. As such, a patient present in a location of a healthcare facility (for instance, a hospital room or a clinical care office examination room) encounters periods of time in which a member of her healthcare team is not present in the location with the patient. By way of example, during an in-patient hospital stay, a patient may encounter lengthy periods of time during which she is monitored by one or more medical devices but not directly observed by a member of her healthcare team. In another example, during an out-patient visit to a clinician's office, a patient may encounter periods of time during which she is waiting in an examination room for the clinician to join her. During times such as these, a patient may require, or desire, something from a healthcare team member, for instance, ice chips, water, pain medication, a change in the room environmental conditions (e.g., temperature), and the like. However, the patient may not know who the appropriate healthcare team member is that can address the concern, may not know where to find the appropriate healthcare team member, or may be unable to leave the room to attempt to find the appropriate healthcare team member (for instance, the patient may be recovering from a procedure and unable to physically leave their present location).

For reasons such as this, locations within a healthcare facility (e.g., hospital, clinical office examination room, or the like) may include a means for the patient to let a healthcare team member know that assistance is required or desired. Such means may include a button or switch that may be activated by the patient that illuminates a light outside of the room to indicate the need or desire for assistance. While this solution permits healthcare team members to know that assistance is requested, it often contains little or no information regarding the nature of the requested assistance. Thus, a healthcare team member must interrupt his or her workflow to go to the patient location or to open an audio channel with the patient (e.g., via telephone or two-way speaker) to find out more information and to discover who the appropriate healthcare team member is to address the concern.

Some means for permitting patients to request assistance include a modicum of information to alleviate some of this disruption. For instance, a patient may have multiple buttons that may be pressed, each indicating a different need or request. In such situations, the assistance indicator provided to the healthcare team (e.g., the illuminated light) may include, for instance, a different colored light for different concerns. While such solutions aid in alleviating the healthcare team members' need for additional information regarding patient assistance calls, other issues remain unaddressed. For instance, until a healthcare team member actually arrives at the patient location or opens an audio channel with the patient, the patient has no way of knowing if anyone is aware that assistance has been requested (that is, if anyone has seen the illuminated light). Additionally, if a healthcare team member addresses the patient concern by opening an audio channel, the team member often still must physically go to the patient location to turn off the illuminated light, generally by pressing a button indicating the concern has been addressed.

In other cases, the means for letting a healthcare team member know that assistance is required or desired may include means that permit the patient to open an audio channel between a device in the room (e.g., via a telephone or two-way speaker) and a device at a central healthcare team member location (e.g., a nursing station) or a device specific to a particular healthcare team member. While this situation is less disruptive to a healthcare team member than the above-mentioned solution as it requires fewer steps to achieve a similar result, it is still disruptive, particularly if the healthcare team member is attending to another matter and unable to address the concern at the moment the audio channel is opened.

Additionally, each time a request for assistance is received and each time a healthcare team member addresses such request, notation may need to be made in a medical record associated with the patient. Such record documentation is time consuming and cumbersome for healthcare team members, particularly when the assistance required or desired is minor in nature (e.g., a request for a glass of water).

SUMMARY

The present technology generally relates to devices, systems, and methods for managing patient requests for assistance in a healthcare facility. In some cases, a personal assistant device may be utilized. In some cases, a personal assistant device may recognize voice commands making it easier both for patients to request assistance and for healthcare team members to adequately address and document patient concerns.

In brief, and at a high level, the present disclosure describes technology that may utilize a personal assistant device (e.g., an AMAZON ECHO or a GOOGLE HOME device) associated with a location in a healthcare facility to receive audible patient requests for assistance and to audibly output healthcare team member responses to patient requests for assistance. Upon a personal assistant device receiving a patient's spoken request for assistance, via a listening component thereof, the received request may be transmitted to a device (e.g., a cellular telephone, tablet device, smart watch, or the like) associated with an appropriate healthcare team member, that is, a healthcare team member associated with the patient from whom the request for assistance is received. In some cases, the patient's spoken request for assistance may be recorded and transmitted to the appropriate healthcare team member as an audio file that the healthcare team member may listen to utilizing his or her device. In some cases, the patient's spoken request for assistance may be translated from speech to text (e.g., utilizing a speech/text conversion service or system) for receipt by the device associated with the appropriate healthcare team member as a text request. However received by the appropriate healthcare team member's device, the team member may review the received request and provide a response thereto. An indication that a response has been provided, that is, that the patient's request has been or is being addressed, may be transmitted to the personal assistant device (or another device associated with the patient from whom the request for assistance was received) and audibly output via a speaker thereof.

Accordingly, many of the problems associated with managing patient requests for assistance in a healthcare facility may be alleviated utilizing the present technology. For instance, when utilizing the present technology, patients may be informed when their requests for assistance are being addressed rather than being left to wonder whether their request has been received. Additionally, healthcare team members may be able to quickly let a patient know that a request for assistance is being addressed, as well as gain an appreciation for how critical a received request for assistance is, without having to disrupt their current workflow for more than a few seconds. Further, a patient having limited mobility may still be able to effectively request assistance without having to locate any type of device on which a button or other assistance indicator must be engaged in order to submit a request for assistance. Still further, patients that have vision difficulty may be able to submit a request for assistance and to receive an indication that a request for assistance is being addressed without having to read any text or otherwise visually engage with a device.

One aspect of the present technology that may accomplish these objectives is a system for managing patient assistance requests in a healthcare facility. The system may include a personal assistant device associated with a location in a healthcare facility and having a listening component and a speaker, the personal assistant device being configured to receive voice commands and to audibly provide responses to received voice commands. The system further may include a processor in communication with the personal assistant device and an Electronic Healthcare Information System (EHIS). Still further, the system may include one or more computer-readable media storing computer-readable instructions that, when executed by the processor, cause the processor to: receive, via the listening component, a voice command from a patient associated, in the EHIS, with the healthcare facility location; transmit the received voice command to a device associated with an appropriate healthcare team member; receive, from the device associated with the appropriate healthcare team member, a response to the voice command; and audibly output, via the speaker, an indication that the response was received from the appropriate healthcare team member associated with the healthcare team member device.

The present disclosure further describes technology that may utilize a personal assistant device associated with a location in a healthcare facility to cancel patient assistance requests. A request for assistance may be received from a patient associated with a location in a healthcare facility (e.g., a hospital room or a clinical care office examination room). In some instances, the request for assistance may be received as a verbal request spoken by the patient and received by a listening component of a personal assistant device associated with the healthcare facility location. Upon a healthcare team member receiving and addressing the request (or committing to address the request), the listening component of the personal assistant device associated with the location in the healthcare facility may receive a voice command (e.g., via the listening component) to cancel the request. In some instances, a source of the voice command may be verified as an approved source that is authorized to cancel the request. By way of example, it may be verified that the voice command is received from a healthcare team member authorized to cancel assistance requests from the patient and not from the patient themselves. By way of example only, such verification may include one or more of verifying a voice signature of the source of the voice command, verifying the location in the healthcare facility that is associated with the personal assistant device as a current location of an approved source utilizing a device enabled with a real-time location system, verifying the source of the voice command as a member of a care team associated with the patient from whom the request for assistance is received, and verifying the source of the voice command via input of an identification credential associated with an approved source. Based upon receipt (and, in some instances, verification of the source) of the voice command, the request for assistance may be cancelled.

As such, many of the problems associated with cancelling patient requests for assistance in a healthcare facility may be alleviated utilizing the present technology. For instance, a healthcare team member may verbally cancel a request for assistance, alerting other healthcare team members that a patient's concern has been or is being addressed, while he or she is performing another task in the healthcare facility location of the patient that submitted the assistance request. In this way, the healthcare team member need not take any additional time than the time it takes to address the patient's request and may quickly and easily cancel the request such that other healthcare team members are aware that the patient's request does not need to be addressed by them.

An aspect of the technology that may accomplish these objectives is a method for cancelling patient assistance requests. The method may include receiving a request for assistance for a patient associated with a location in a healthcare facility; receiving, via a listening component of a personal assistant device associated with the location in the healthcare facility, a voice command from a healthcare team member to cancel the request for assistance; verifying the healthcare team member as an approved source that is authorized to cancel the request; and upon verification of the healthcare team member as an approved source, cancelling the request for assistance.

Still further, the present disclosure describes technology that may utilize a personal assistant device associated with a location in a healthcare facility to receive audible documentation items from healthcare team members for inputting into patient medical records associated with an EHIS. A voice command may be received from a healthcare team member via a listening component associated with a personal assistant device. In some cases, the voice command may include at least one item to be documented in association with a patient's medical records associated with an EHIS. Upon receipt of the voice command, the identity of the healthcare team member may be verified, at least in part, utilizing information associated with the EHIS. In some instances, such information may include, by way of example only, one or more of a voice signature of the healthcare team member, a location of the healthcare team member received from a device enabled with a real-time location system, identification of the healthcare team member as a member of the care team associated with the patient, and input of an identification credential associated with the healthcare team member. Upon verification of the healthcare team member's identity, the at least one item may be documented in the EHIS, for instance, in a medical record associated with the patient. In some instances, the received voice command containing the at least one item for documentation may be translated from speech to text prior to documentation in the EHIS. In some instances, an identity of the patient for whom the at least one item is to be documented may be determined, for instance, utilizing information included in the EHIS and/or location-based awareness.

As such, many of the problems associated with documenting items in a healthcare facility, particularly minor, routine, and/or frequently-performed items, may be alleviated utilizing the present technology. For instance, healthcare team members responding to requests directed to the comfort of a patient (e.g., requests for ice chips, water, an environmental condition change, and the like) may quickly and easily document their response to the request, often times as the request is being addressed. By way of example, as a healthcare team member is delivering a glass of water to a patient in response to a patient request, he or she may verbally document that the patient was given a glass of water and the time without having to log-in to a computer, locate and open the patient's chart, and document the event—all of which can be cumbersome and time consuming tasks.

One aspect of the present technology that may accomplish these objectives is a system for documenting items in a healthcare facility. The system may include a personal assistant device associated with a location in a healthcare facility and having a listening component and a speaker, the personal assistant device being configured to receive voice commands and to audibly provide responses to received voice commands. The system further may include a processor in communication with the personal assistant device and an EHIS. Still further, the system may include one or more computer-readable media storing computer-readable instructions that, when executed by the processor, cause the processor to: receive, via the listening component, a voice command from a healthcare team member, the voice command including at least one item to be documented in an EHIS in a medical record associated with a patient; verify an identity of the healthcare team member using, at least in part, information associated with the EHIS; and upon verification of the identity of the healthcare team member, document the at least one item in the EHIS, for instance, in the medical record associated with the patient.

Additional objects, advantages, and novel features of the technology are described below in the Detailed Description. They will, in part, become apparent to those skilled in the art, or they may be learned by practice of the technology.

BRIEF DESCRIPTION OF THE DRAWINGS

The present technology is described in the Detailed Description with reference to the attached figures, wherein.

DETAILED DESCRIPTION

The subject matter of the present technology is described herein with specificity to meet statutory requirements. However, the description itself is not intended to limit the scope of this disclosure. Rather, the inventors have contemplated that the claimed subject matter also might be embodied in other ways, to include different steps or combinations of steps similar to the ones described in this document, in conjunction with other present or future technologies. Moreover, although the term "step" may be used herein to connote different elements of methods employed, the term should not be interpreted as implying any particular order among or between various steps disclosed, unless the order of individual steps is explicitly described.

Embodiments of the present technology are directed to methods, systems, and computer-readable media for utilizing personal assistant devices to manage patient assistance requests in a healthcare facility, documenting items (e.g., minor, routine, and/or frequently-performed items) in association with a patient's records in an Electronic Healthcare Information System (EHIS), and cancelling patient requests for assistance. Certain aspects may provide for audibly outputting, from a speaker associated with a personal assistant device, an indication that a request for assistance has been received and/or is being addressed by an appropriate healthcare team member. Certain aspects also may provide for permitting healthcare team members to verbally provide items for documentation in association with a patient's medical records, the items for documentation being received by a listening component of a personal assistant device and transmitted to an EHIS for documentation. Aspects also may permit healthcare team members to verbally cancel patient requests for assistance upon the healthcare team member addressing the request and, in some instances, verification of the healthcare team member as an approved source for documenting the item(s) in association with the patient. Further aspects and embodiments are described in detail below.

Figure 1:
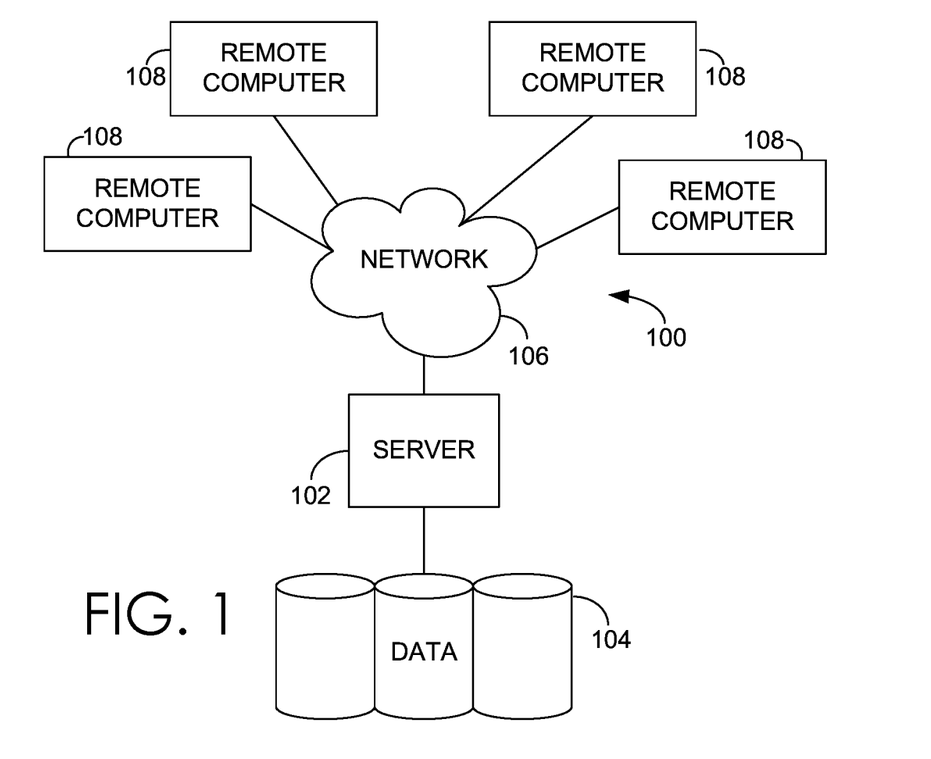
FIG. 1 is a block diagram of an exemplary computing environment suitable for implementing aspects of the technology in accordance with aspects hereof.

With reference now to FIG. 1, an exemplary computing environment suitable for use in implementing aspects of the technology is described below. An exemplary computing environment (e.g., a medical-information computing-system environment) with which embodiments may be implemented is provided. The computing environment is merely an example of one suitable computing environment and is not intended to suggest any limitation as to the scope of use or functionality of the technology. Neither should the computing environment be interpreted as having any dependency or requirement relating to any single component or combination of components illustrated therein.

The present technology may be operational with numerous other general or special purpose computing system environments or configurations. Examples of well-known computing systems, environments, and/or configurations that may be suitable for use with aspects of the present technology include personal computers, server computers, hand-held or laptop devices, multiprocessor systems, microprocessor-based systems, set top boxes, programmable consumer electronics, network PCs, minicomputers, mainframe computers, personal assistant devices, distributed computing environments that include any of the above-mentioned systems or devices, and the like.

The present technology may be described in the general context of computer-executable instructions, such as program modules, being executed by a computer. Exemplary program modules include routines, programs, objects, components, and data structures that perform particular tasks or implement particular abstract data types. The present technology may be practiced in distributed computing environments where tasks are performed by remote processing devices that are linked through a communications network. In a distributed computing environment, program modules may be located in association with local and/or remote computer storage media (e.g., memory storage devices).

The computing environment comprises a computing device in the form of a control server 102. Exemplary components of the control server 102 comprise a processing unit, internal system memory, and a suitable system bus for coupling various system components, including data stores, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes, or has access to, a variety of non-transitory computer-readable media. Computer-readable media can be any available media that may be accessed by the control server 102, and includes volatile and non-volatile media, as well as, removable and non-removable media. By way of example, and not limitation, computer-readable media may comprise computer storage media and communication media. Computer storage media includes volatile, non-volatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above also should be included within the scope of computer-readable media.

The control server 102 may operate in a computer network using logical connections to one or more remote computers 108. The remote computers 108 may be located at a variety of locations including operating systems, device drivers and medical information workflows. The remote computers also may be physically located in traditional and nontraditional medical care environments so that the entire healthcare community may be capable of integration on the network. The remote computers might be personal computers, servers, routers, network PCs, peer devices, other common network nodes, or the like and might comprise some or all of the elements described above in relation to the control server 102. The devices can be personal digital assistants or other like devices.

The computer network 106 may comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof may be stored in association with the control server 102, the data store 104, or any of the remote computers 108. For example, various application programs may reside on the memory associated with any one or more of the remote computers 108. It will be understood and appreciated by those of ordinary skill in the art that the network connections shown are exemplary and other means of establishing a communications link between the computers (e.g., the control server 102 and the remote computers 108) may be utilized.

In operation, an organization may enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information also may be sent directly from a remote healthcare device to the control server 102. In addition to a monitor, the control server 102 and/or the remote computers 108 may comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
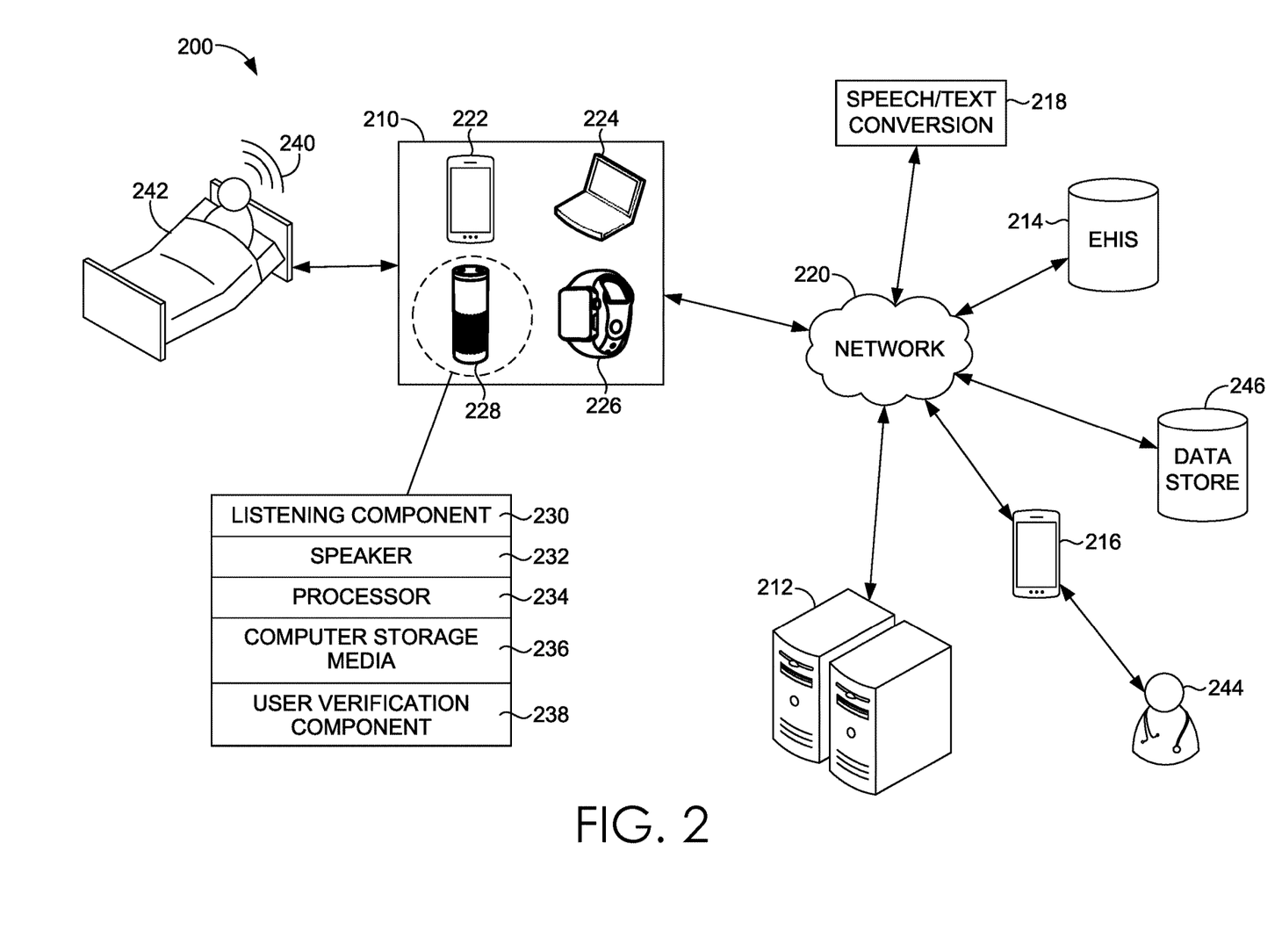
FIG. 2 is a block diagram of an exemplary system for managing patient assistance requests, documenting items in a healthcare facility, and/or cancelling patient assistance requests, in accordance with aspects hereof.

Turning now to FIG. 2, illustrated is a block diagram of an exemplary system 200 for utilizing personal assistant devices to manage patient assistance requests in a healthcare facility, documenting items (e.g., minor, routine, and/or frequently-performed items) in association with patients' records in an EHIS, and cancelling patient requests for assistance. In the illustrated aspect, the system comprises a patient communication device 210, a control component 212, an Electronic Healthcare Information System (EHIS) 214, a healthcare team member device 216, and a speech/text conversion component 218, all in communication with one another through a network 220. The network 220 may be any type of communication scheme that allows devices to exchange data. For example, the network 220 may include fiber optic, wired and/or wireless communication capability in any of a plurality of protocols, such as TCP/IP, Ethernet, WAP, IEEE 802.11, or any other protocols. Implementations are contemplated in which the system 200 may be accessible through a shared public infrastructure (e.g., the Internet), an extranet, an intranet, a virtual private network (VPN), a local area network (LAN), a wide area network (WAN), a peerto-peer (P2P) network, a wireless communications network, a telephone network, a facsimile network, a cloud network, or any combination thereof. Such networks are commonplace in today's computing environments and, accordingly, are not further described herein. Although many of the components illustrated in FIG. 2 are described as individual components or functional entities, in some cases, they may be implemented as discrete or distributed components, or in conjunction with other components, having any suitable location or combination.

The system 200 includes a patient communication device 210. The patient communication device 210 may include devices such as a mobile phone 222 or a laptop computer 224. The patient communication device 210 may include other types of mobile devices, such as a tablet, or wearables, such as a smart watch 226, in accordance with aspects of the present technology. In some aspects, the patient communication device 210 may include a personal assistant device 228. Personal assistant devices are a category of smart speakers that enable users to speak voice commands to interact with a personal assistant service that aids the user in obtaining answers to questions and/or in completing certain tasks. Exemplary personal assistant devices include, without limitation, AMAZON ECHO which utilizes a personal assistant service referred to as "Alexa" and GOOGLE HOME, which utilizes a personal assistant service referred to as "Google Assistant." As illustrated, the personal assistant device 228 includes a listening component 230, a speaker 232, a processor 234, computer storage media 236, and a user verification component 238. The listening component 230 may be configured for detecting an audible signal 240, for example a voice command from a user (e.g., a patient-user 242 and/or a healthcare-team-member-user 244) associated with a location in a healthcare facility. One common example of a type of listening component 230 is a microphone. In some aspects (not shown), the listening component 230 may be a separate component that is communicatively coupled, for example, by hardwire or wirelessly, to the personal assistant device 228.

In general, any person could be considered a user of the system 200. In a non-limiting example, the user may be a patient 242 present in a location of a healthcare facility (for instance, a hospital room or a clinical care office examination room). The audible signal 240 may be a voice command, such as a command indicating that the patient-user 242 requires assistance from an appropriate healthcare team member (e.g., healthcare team member 244). Patient requests for assistance may include, without limitation, a request to use the bathroom, a request for pain medication, a request for water, a request for ice chips, a request for food, a request to adjust location environmental conditions (e.g., temperature), or a general request for healthcare team member assistance. In another non-limiting example, the user may be a healthcare-team-member-user 244. In such instances, the audible signal 240 may be a voice command, such as a command to cancel a patient request for assistance or a command to document an action in the EHIS 214, e.g., in a record associated with a patient.

In some aspects, the audible signal 240 may be in the form of a question. In some aspects, initial utterance of the audible signal 240 may include a "wake word," that is, a word that alerts the personal assistant device 228 that the user 242 or 244 is speaking a voice command intended for the device 228. By way of non-limiting example, the wake word generally utilized with the AMAZON ECHO personal assistant device is "Alexa" and the wake word generally utilized with the GOOGLE HOME personal assistant device is "Google." In a non-limiting example, after the wake word signals the personal assistant device 228 that a request intended for the device is to follow, the user (e.g., the patient-user 242 or the healthcare-team-member-user 244) may speak an utterance (e.g., a statement) to invoke their intent. As used in this context, an "intent" represents an action that fulfills the user's spoken request.

By way of example, assume the patient-user 242 is utilizing an AMAZON ECHO personal assistant device and that she desires to utilize the personal assistant device 242 to request a glass of water. The patient-user 242 in this instance may speak one of a number of utterances that the personal assistant device is programmed to recognize as associated with a "NeedsAssistance" intent. For instance, the user may in this instance utter "May I have a glass of water?" or "Can I have water?". In some instances, intents can have "slots" that the user may customize to request fulfillment of a particular request. For instance, utilizing the above example, the user 202 may utter "Can I have {Item}?" In this instance, the user would speak the name of the desired item in the "slot" indicated as {Item}. The user may utilize a similar spoken format to fulfill other intents as well. An exemplary response from the personal assistant device 210 in each of the delineated instances may be "Your request is being addressed by Nurse Jones and someone will be with you shortly."

The speaker 232 of the personal assistant device 228 may be configured to provide audible output to the user (e.g., the patient-user 242 or the healthcare-team-member-user 244). By way of example, the speaker 232 may provide an indication of a healthcare team member response to a voice command received by the listening component 230 of the personal assistant device 228. For instance, if the personal assistant device 228 is an AMAZON ECHO device, the patient-user 242 may speak the exemplary voice command "Alexa, may I have a glass of water?" Once an appropriate healthcare team member has addressed the request, the speaker 232 may audibly output a message to the patient-user 242, for instance, the speaker 232 may audibly output the message "Nurse Jones has received your request and will be with you shortly." In some aspects (not shown), the speaker 232 may be a component separate from the personal assistant device 228 that is communicatively coupled, for example, by hardwire or wirelessly, to the personal assistant device 228.

In some aspects, a voice command may require information in addition to the wake word in order to appropriately route (as more fully described below) the user's request. For instance, the voice command may require information associated with the EHIS 214 in order to be appropriately routed. By way of example, the patient-user 242 may utter the voice command "Alexa, ask my healthcare team member if I may have a glass of water." In such an instance, the utterance of "my healthcare team member" alerts the personal assistance device service as to whom the request is to be routed or to which role the individual to whom the request is to be routed fills such that the system 200 may query the EHIS 214 for such information.

In exemplary aspects, the speaker 232 may be configured to provide confirmation that a particular voice command 240 has been performed or to provide feedback that a particular voice command 240 is being performed. In some exemplary aspects, the speaker 232 may be configured to prompt the user (e.g., the patient-user 242 or the healthcare-team-member-user 244) for more information or convey to the user that a received voice command 240 is invalid.

The processor 234 of the personal assistant device 228 may be any type of hardware programmed to perform the functions described herein below. For instance, in some embodiments, the processor 234 is a general purpose processor executing instructions stored in memory (not shown). In other embodiments, the processor 234 comprises a special purpose logic component. For example, and without limitation, illustrative types of special purpose logic components that can be used include Field Programmable Gate Arrays (FPGAs), Application-Specific Integrated Circuits (ASICs), Application-specific Standard Products (ASSPs), System-On-a-Chip (SOCs), Complex Programmable Logic Devices (CPLDs), and the like.

Other components of the personal assistant device 210, such as the computer storage media 236 may be similar to those described with respect to the exemplary computing environment of FIG. 1.

The processor 234 and the computer storage media 236 generally operate to route received voice commands 240 to the appropriate healthcare team member device 216 and/or the EHIS 214. In some cases, the processor 234 and the computer storage media 236 operate to route received voice commands 240 to the speech/text conversion system or service 218 such that text commands rather than (or in addition to) voice commands may be routed to the appropriate healthcare team member device 216 and/or the EHIS 214.

Aspects of the present technology contemplate utilizing a personal assistant device (e.g., the personal assistant device 228) to output information through the speaker 232. The Health Insurance Portability and Accountability Act of 1996 (HIPAA) includes a Privacy Rule (The Standards for Privacy of Individually Identifiable Healthcare Information) that protects the disclosure of individuals' "protected health information." To facilitate compliance with the HIPAA Privacy Rule, and to otherwise protect sensitive information associated with a patient-user 242, the personal assistant device 228 may further include a user verification component 238. The user verification component 238 may be configured to verify the identity of a particular user, for instance, the patient-user 242 and/or the healthcare-team-member-user 244, before audibly outputting (e.g., via the speaker 232) any sensitive and/or protected health information. By way of example only, a particular user's identity may be verified by voice and/or by authorization code. For instance, a particular user has a distinct voice signature that may be pre-associated with the particular user in a data store, for example, the data store 246 or a data store associated with the EHIS 214 (not shown). When the listening component 230 of the personal assistant device 228 detects the distinct voice signature, the user verification component 238 may associate the voice signature with the particular user, thereby, verifying the particular user. In another case, verification may be performed using an authorization code, such as a password or PIN number. The code may be predetermined and stored in association with a particular user (e.g., in the data store 246 or in a data store (not shown) associated with the EHIS 214). When the listening component 230 of the personal assistant device 228 detects the code, the user verification component 238 may associate the code with the particular user to verify the user. It will be understood and appreciated by those having ordinary skill in the art that other means of verifying a user's identity are available and are continually being developed. Any and all such existing and future means of user verification are contemplated to be within the scope of aspects of the present technology. In some aspects (not shown), the user verification component 238 may be a component separate from the personal assistant device 228 that is communicatively coupled, for example, by hardwire or wirelessly, to the personal assistant device 238.

With continued reference to FIG. 2, the system 200 includes a control component 212. The control component 212 may be configured to determine appropriate routing for received requests/responses. For instance, the control component 212 may be configured to receive requests for assistance (e.g., from the personal assistant device 228), receive responses to requests for assistance (e.g., from the healthcare-team-member device 216) and determine whether the requests/responses require speech/text conversion (e.g., by the speech/text conversion component 218 (more fully described below)). In embodiments, requests for assistance and responses thereto may be received by the control component 212 as audio files and/or as text files. By way of example, the control component 212 may be configured to receive an audio file request from the patient-user 242, determine that the received request is to be routed both to the healthcare team member 244 as an audio file and to the speech/text conversion component 218 for conversion from the audio file to a text file and then to the EHIS for documentation in association with medical records associated with the patient-user 242. In another instance, the control component 212 may determine that a text file response to a patient request received from the healthcare team member 244 is to be routed to the speech/text conversion component for conversion from text to speech and subsequently to the personal assistant device 228 associated with the patient from whom the request was received for outputting by the speaker. In this instance, the control component 212 further may determine that the text file is to be routed to the EHIS 214 for storage.

Continuing reference to FIG. 2, the system 200 includes a speech/text conversion component 218 communicatively coupled with the network 220. By way of example, the speech/text conversion component 218 may be configured to convert audible signals (such as the audible signal 240) into readable text and/or vice versa. The readable text may be human readable or machine readable, as appropriate. By way of example, the speech/text conversion component 218 may be configured to convert readable text into audible signals for output by the speaker 232 of the personal assistant device 228. For instance, the speech/text conversion component 218 may be configured to convert human readable text including an indication of a response to a patient request for assistance into audible signals for audibly providing the same to the user 240 via the speaker 232 of the personal assistant device 228. Additionally, the speech/text conversion component 218 may be configured to convert audible signals, e.g., the audible signal 240, into text, for instance, for storage in association with the EHIS 214, for instance, in association with a patient-user's medical records.

Figure 3:
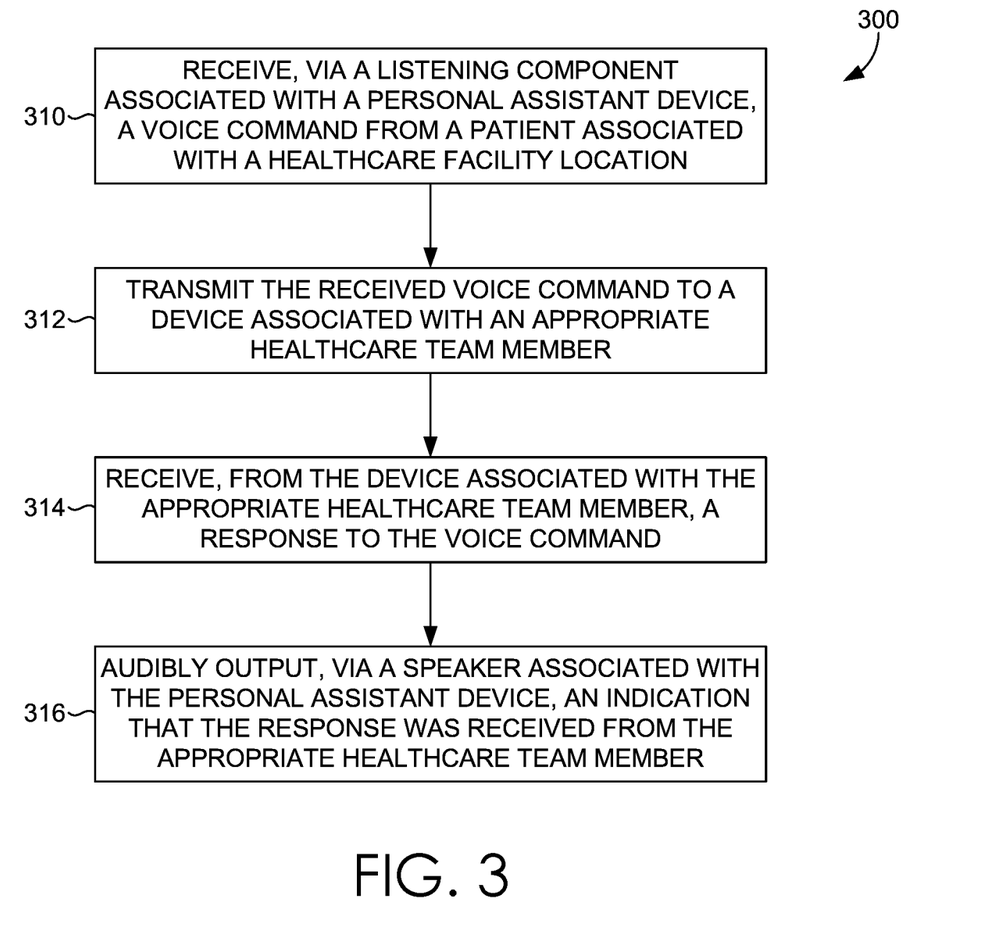
FIG. 3 is a block diagram of an exemplary method for managing patient assistance requests in a healthcare facility in accordance with aspects hereof.

With reference now to FIG. 3, a block diagram is illustrated of an exemplary method 300 for managing patient assistance requests in a healthcare facility. At block 310, a voice command is received from a patient (e.g., the voice command 240 is received from the patient-user 242 of FIG. 2). The patient is associated, in an electronic healthcare information system (e.g., the EHIS 214 of FIG. 2), with a healthcare facility location and the voice command is received from a personal assistant device (e.g., the personal assistant device 228 of FIG. 2) associated with the healthcare facility location. In some configurations, the personal assistant device includes a listening component (e.g., a microphone or other type of sensor that converts sound into electrical signals, e.g., the listening component 230 of FIG. 2) and a speaker (e.g., the speaker 232 of FIG. 2).

At block 312, the received voice command is transmitted (e.g., via the network 220 of FIG. 2) to a device (e.g., the device 216 of FIG. 2) associated with an appropriate healthcare team member (e.g., the healthcare team member 244 of FIG. 2). In embodiments, the appropriate healthcare team member is determined (for instance, by the control component 212 of FIG. 2), based at least in part, on information associated with an electronic healthcare information system (e.g., the EHIS 214 of FIG. 2). In embodiments, the received voice command is translated from speech to text (e.g., by the speech/text conversion component 218 of FIG. 2) and the translated voice command is transmitted to the device (e.g., the healthcare team member device 216 of FIG. 2) associated with the appropriate healthcare team member (e.g., the healthcare team member 244 of FIG. 2). In embodiments the received voice command is recorded and the recorded voice command is audibly provided to the appropriate healthcare team member device (e.g., the healthcare team member device 216 of FIG. 2) associated with the healthcare team member (e.g., the healthcare team member 244 of FIG. 2) without the need for speech-to-text conversion.

At block 314, a response to the voice command is received (e.g., by the personal assistant device 228 of FIG. 2) from the device (e.g., the device 216 of FIG. 2) associated with the appropriate healthcare team member (e.g., the healthcare team member 244 of FIG. 2). At block 316, an indication that the response was received from the appropriate healthcare team member (e.g., the healthcare team member 244 of FIG. 2) associated with the healthcare team member device (e.g., the healthcare team member device 216 of FIG. 2) is audibly output via the speaker (e.g., the speaker 232 of FIG. 2) of the personal assistant device (e.g., the personal assistant device 228 of FIG. 2). In embodiments, the indication that the response was received is automatically generated when the request is heard or read by an appropriate healthcare team member. In embodiments, the indication that the response was received includes the response to the voice command. In such embodiments, if the response to the voice command is received as a text response, the text response may be translated into a voice response (e.g., utilizing the speech/text conversion component 218 of FIG. 2). In embodiments, the response to the voice command may be selected by the appropriate healthcare team member (e.g., the healthcare team member 244) from a plurality of common responses.

In embodiments, at least one of the received voice command (or a textual translation thereof) and the indication that the response was received from the appropriate healthcare team member (e.g., the healthcare team member 244 of FIG. 2) associated with the healthcare team member device (e.g., the healthcare team member device 216 of FIG. 2) is stored in the electronic healthcare information system (e.g., the EHIS 214 of FIG. 2) and associated with the patient (e.g., the user 242 of FIG. 2).

Figure 4:
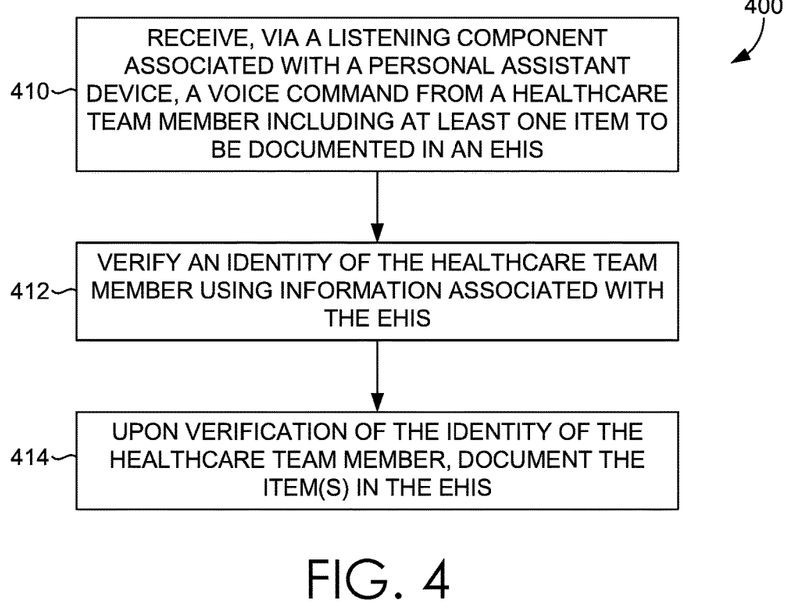
FIG. 4 is a block diagram of an exemplary method for documenting items in a healthcare facility in accordance with aspects hereof.

Turning to FIG. 4, a block diagram is illustrated of an exemplary method 400 for documenting items in a healthcare facility. At block 410, a voice command is received via a listening component (e.g., the listening component 230 of FIG. 2) of a personal assistant device (e.g., the personal assistant device 228 of FIG. 2) from a healthcare team member (e.g., the healthcare-team-member-user 244 of FIG. 2). The voice command includes at least one item to be documented in an electronic healthcare information system (e.g., the EHIS 214 of FIG. 2) in a medical record associated with a patient (e.g., the patient-user 242 of FIG. 2). In embodiments, an identity of the patient (e.g., the patient-user 242 of FIG. 2) is determined, at least in part, utilizing information associated with an electronic healthcare information system (e.g., the EHIS 214 of FIG. 2). In embodiments, an identity of the patient (e.g., the patient-user 242 of FIG. 2) is determined, at least in part, utilizing location-based awareness.

At block 412, an identity of the healthcare team member (e.g., the healthcare-team-member-user 244 of FIG. 2) is verified. The identity is verified using, at least in part, information associated with an electronic healthcare information system (e.g., the EHIS 214 of FIG. 2). In embodiments, the information associated with the electronic healthcare information system (e.g., the EHIS 214 of FIG. 2) includes one or more of a voice signature of the healthcare team member, a location of the healthcare team member received from a device enabled with a real-time location system, identification of the healthcare team member as a member of a care team associated with the patient, and input of an identification credential associated with the healthcare team member.

At step 414, upon verification of the identity of the healthcare team member (e.g., the healthcare-team-member-user 244 of FIG. 2), the at least one item is documented in the electronic healthcare information system (e.g., the EHIS 214 of FIG. 2) in the medical record associated with the patient (e.g., the patient-user 242 of FIG. 2). In embodiments, the received voice command is converted (e.g., utilizing the speech/text conversion service/system 218 of FIG. 2) into a text command prior to documenting the item(s) in the electronic healthcare information system (e.g., the EHIS 214 of FIG. 2) in the medical record associated with the patient (e.g., the patient-user 242 of FIG. 2).

Figure 5:
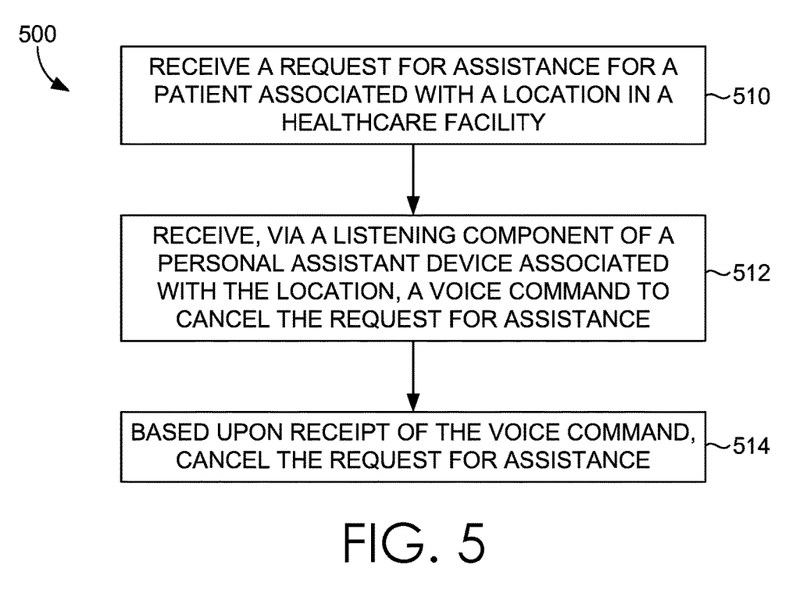
FIG. 5 is a block diagram of an exemplary method for cancelling patient assistance requests in accordance with aspects hereof.

With reference to FIG. 5, a block diagram is illustrated of an exemplary method 500 for cancelling patient assistance requests. At block 510, a request for assistance is received for a patient (e.g., the patient-user 242 of FIG. 2) associated with a location in a healthcare facility. In embodiments, the request for assistance for the patient associated with the location in the healthcare facility is received via the listening component (e.g., the listening component 230 of FIG. 2) of the personal assistant device (e.g., the personal assistant device 228 of FIG. 2) associated with the location in the healthcare facility.

At block 512, a voice command to cancel the request for assistance is received, via a listening component (e.g., the listening component 230) of a personal assistant device (e.g., the personal assistant device 228 of FIG. 2) associated with the location in the healthcare facility. In embodiments, the source of the voice command to cancel the request for assistance is verified (e.g., utilizing the user verification component 238 of the personal assistant device 228 of FIG. 2) as an approved source authorized to cancel the request for assistance.

In embodiments, the source of the voice command to cancel the request for assistance as an approved source comprises verifying the source of the voice command to cancel the request for assistance utilizing, at least in part, information associated with an electronic healthcare information system (e.g., the EHIS 214 of FIG. 2). In embodiments, the source of the voice command to cancel the request for assistance as an approved source comprises verifying the source of the voice command utilizing one or more of a voice signature of the source of the voice command, a location of the source using a device enabled with a real-time location system, identification of the source of the voice command as a member of a healthcare team associated with the patient, and input of an identification credential associated with the source.

At block 514, based upon receipt of the voice command to cancel the request for assistance, the request for assistance is cancelled. In embodiments, at least one of the indication of the request for assistance and an indication of the cancellation of the request for assistance is documented in a medical record associated with the patient in an electronic healthcare information system (e.g., the EHIS 214 of FIG. 2).

From the foregoing, it will be seen that this technology is one well adapted to attain all the ends and objects described, and together with other advantages which are obvious and inherent to the structure. It will be understood that certain features and subcombinations are of utility and may be employed without reference to other features and subcombinations. This is contemplated by and is within the scope of the claims. Since many possible embodiments may be made of the present technology without departing from the scope, it is to be understood that all matter described or shown in the accompanying drawings is to be interpreted as illustrative and not in a limiting sense.

What is claimed is:

1. A system for documenting items in a healthcare facility, the system comprising:
   a personal assistant device associated with a location in a healthcare facility and having a listening component and a speaker, the personal assistant device being configured to receive voice commands and to audibly provide responses to received voice commands;
   a processor configured to communicate with the personal assistant device and to communicate with an electronic healthcare information system; and
   one or more computer-readable media storing computer-readable instructions that, when executed by the processor, cause the processor to:
      receive, via the listening component, a voice command from a healthcare team member that is provided in response to a request for assistance from a patient;
      verify an identity of the healthcare team member by, at least in part, (i) detecting a voice signature from the voice command and (ii) associating the voice signature to a particular user based on matching the voice signature to one of a plurality of distinct voice signatures that are associated to individual users associated with the electronic healthcare information system;
      determine whether the voice command includes at least one item to be documented in the electronic healthcare information system in a medical record associated with the patient;
      determine whether the voice command includes a command to cancel the request for assistance from the patient;
      in response to determining the voice command includes at least one item to be documented, document the at least one item from the voice command in the electronic healthcare information system in the medical record associated with the patient;
      in response to determining the voice command includes the command to cancel the request for assistance, (i) cancelling the request for assistance within the electronic healthcare information system; and
      (ii) generating and transmitting, by the processor, an alert to one or more devices of healthcare team members in the healthcare facility, wherein the alert indicates that the request for assistance has been addressed.

2. The system of claim 1, wherein the computer-readable instructions to verify the identity of the healthcare team member is based on information associated with the electronic healthcare information system that includes at least a voice signature of the healthcare team member, a location of the healthcare team member received from a device enabled with a real-time location system, and an identification of the healthcare team member as a member of a care team associated with the patient.

3. The system of claim 1, wherein when executed by the processor, the computer-readable instructions further cause the processor to translate the received voice command into a text command prior to documenting the at least one item in the electronic healthcare information system in the medical record associated with the patient.

4. The system of claim 1, wherein when executed by the processor, the computer-readable instructions further cause the processor to:
   receive, via the personal assistant device, a voice request from a patient;
   determine an identity of the patient by, at least in part, detecting a voice signature from the voice request and associating the voice signature to a particular patient based on matching the voice signature to one of a plurality of distinct voice signatures that are associated to patients that are associated with the electronic healthcare information system.

5. The system of claim 1, wherein when executed by the processor, the computer-readable instructions further cause the processor to determine the identity of the healthcare team member by detecting the voice signature from the voice command that is a distinct voice signature based on voice and is not based on recognized words.

6. A method performed by a computing system including at least one processor, the method comprising:
   receiving, via a personal assistant device including a listening component and a speaker, a voice request from a patient;
   wherein the personal assistant device is positioned in a healthcare facility in proximity to the patient and is connected via a network to the computing system;
   identifying the voice request as a request for assistance based on at least recognizing verbal content of the voice request;
   transmitting the voice request, via network communications, to a device associated with a healthcare team member, wherein the voice request causes the healthcare team member to provide a voice response to the voice request;
   in response to the computing system receiving the voice response to the voice request, verifying an identity of the healthcare team member by, at least in part, (i) detecting a distinct voice signature from the voice response wherein the distinct voice signature is not an identification word from the voice response and (ii) associating the distinct voice signature to a particular user based on matching the distinct voice signature to one of a plurality of distinct voice signatures that are assigned to individual users and stored in a data store;
   determining whether the voice response includes at least one item to be documented in an electronic healthcare information system in a medical record associated with the patient;

determining whether the voice response includes a command to cancel the voice request for assistance from the patient;

upon verification of the identity of the healthcare team member and in response to determining the voice response includes at least one item to be documented, transmitting and storing at least a portion of content from the voice response into the medical record associated with the patient; and upon verification of the identity of the healthcare team member and in response to determining the voice response includes the command to cancel the request for assistance:
  (i) cancelling the request for assistance within the electronic healthcare information system; and
  (ii) generating and transmitting, by at least the processor, an alert to one or more devices of healthcare team members in the healthcare facility, wherein the alert indicates that assistance for the voice request has been provided.

7. The method of claim 6, further comprising:
receiving the voice response to the voice request by the listening component of the personal assistant device; and
wherein detecting the distinct voice signature from the voice response is based on voice properties of the healthcare team member and is not based on recognized words from the voice response.

8. The method of claim 6, wherein verifying the identity of the healthcare team member further comprising:
comparing the distinct voice signature from the voice response to the plurality of distinct voice signatures from the data store to identify a match.

9. The method of claim 6, wherein verifying the identity of the healthcare team member further comprising:
detecting a code from content of the voice response; and
comparing the code to stored codes in the data store, wherein each of the stored codes is associated with a particular user.

10. The method of claim 6, further comprising:
determining an identity of the patient by, at least in part:
(i) detecting a voice signature from the voice request; and
(ii) associating the voice signature to a particular patient based on matching the voice signature to one of a plurality of distinct voice signatures that are associated to patients that are associated with the electronic healthcare information system.

11. The method of claim 6, wherein identifying the voice request as a request for assistance based on at least recognizing verbal content of the voice request further comprises:
recognizing a wake word from the verbal content of the voice request that alerts the personal assistant device that the patient is making a request for assistance.

12. A non-transitory computer-readable media storing computer-executable instructions that, when executed by a processor of a computing system, cause the processor to:
receive, via a personal assistant device, a voice command from a healthcare team member, wherein the voice command is provided in response to a request for assistance from a patient;

wherein the personal assistant device is associated with a location in a healthcare facility and is configured with a listening component and a speaker;

verify an identity of the healthcare team member by, at least in part:
  (i) detecting a voice signature from the voice command and
  (ii) associating the voice signature to a particular user based on matching the voice signature to one of a plurality of distinct voice signatures that are associated to individual users associated with an electronic healthcare information system;

determine whether the voice command includes at least one item to be documented in the electronic healthcare information system in a medical record associated with the patient;

determine whether the voice command includes a command to cancel the request for assistance from the patient;

upon verification of the identity of the healthcare team member and in response to determining the voice command includes at least one item to be documented, store the at least one item from the voice command in the electronic healthcare information system in the medical record associated with the patient; and upon verification of the identity of the healthcare team member and in response to determining the voice command includes the command to cancel the request for assistance:
  (i) cancel the request for assistance within the electronic healthcare information system; and
  (ii) generate and transmit, by at least the processor, an alert to one or more devices of healthcare team members in the healthcare facility, wherein the alert indicates that assistance for the request for assistance has been provided.

13. The non-transitory computer-readable media of claim 12, further comprising computer-executable instructions configured to cause the processor to:
detect and recognize a wake word that alerts the personal assistant device that the voice command that follows the wake word is intended as a command for the personal assistant device.

14. The non-transitory computer-readable media of claim 12, wherein the computer-readable instructions to verify the identity of the healthcare team member further perform operations of:
detecting the voice signature from the voice command based on an audible voice of the healthcare team member, wherein the voice signature is not based on recognized words.

* * * * *